(12) United States Patent
Harshbarger (10) Patent No.: US 9,161,470 B2
(45) Date of Patent: Oct. 13, 2015

(54) SENSORS AND SENSOR INTERFACE SYSTEMS

(71) Applicant: Cummins Emission Solutions Inc., Columbus, IN (US)

(72) Inventor: Daniel R Harshbarger, Columbus, IN (US)

(73) Assignee: CUMMINS EMISSION SOLUTIONS INC, Columbus, IN (US)

( * ) Notice: Subject to any disclaimer, the term of this patent is extended or adjusted under 35 U.S.C. 154(b) by 271 days.

(21) Appl. No.: 13/754,710

(22) Filed: Jan. 30, 2013

(65) Prior Publication Data

US 2013/0194757 A1 Aug. 1, 2013

Related U.S. Application Data

(60) Provisional application No. 61/592,803, filed on Jan. 31, 2012.

(51) Int. Cl.
*H05K 1/00* (2006.01)
*H05K 7/02* (2006.01)
*F02M 1/00* (2006.01)

(52) U.S. Cl.
CPC ... *H05K 7/02* (2013.01); *F02M 1/00* (2013.01)

(58) Field of Classification Search
USPC .......................... 361/737, 767, 760, 721, 748
See application file for complete search history.

(56) References Cited

U.S. PATENT DOCUMENTS

| | | | |
|---|---|---|---|
| 6,136,170 A | 10/2000 | Inoue et al. | |
| 6,334,352 B1 | 1/2002 | Poggio et al. | |
| 7,209,999 B2 * | 4/2007 | Jamp et al. | 710/315 |
| 7,722,362 B2 * | 5/2010 | Frake et al. | 439/76.1 |
| 2003/0088346 A1 * | 5/2003 | Calkins et al. | 701/29 |
| 2003/0155238 A1 | 8/2003 | Hada et al. | |
| 2004/0094138 A1 | 5/2004 | Yasui et al. | |
| 2005/0178675 A1 | 8/2005 | Hall | |
| 2009/0021529 A1 * | 1/2009 | Wendler et al. | 345/619 |
| 2009/0056416 A1 | 3/2009 | Nair et al. | |
| 2009/0120668 A1 * | 5/2009 | Fjelstad et al. | 174/250 |
| 2011/0238281 A1 | 9/2011 | Sparks et al. | |
| 2011/0303200 A1 | 12/2011 | Zeitoun | |

OTHER PUBLICATIONS

International Search Report/Written Opinion; PCT/US2013/023922.
Overvoltage protection for sensitive amplifier applications—Part 1; Planet Analog Dec. 7, 2006.
Overvoltage protection for sensitive amplifier application—Part 2; Planet Analog Dec. 11, 2006.
Palatnik et al.; High-impedance buffer amplifier's input includes ESD protection; Sep. 28, 2006.
Falin, Jeff; Reverse Current/Battery Protection Circuit, Texas Instruments; Application Reports; SLVA 139—Jun. 2003.

* cited by examiner

*Primary Examiner* — Hung S Bui
(74) *Attorney, Agent, or Firm* — Taft, Stettinius & Hollister LLP

(57) ABSTRACT

An apparatus, comprising a housing; a first connector coupled to the housing and having a first plurality of contacts; a second connector coupled to the housing and having a second plurality of contacts; and a circuit electrically connected to at least one of the first contacts and at least one of the second contacts. The circuit is encapsulated within the housing. The circuit is configured to generate an output signal in response to a resistance sensed at the at least one of the first contacts.

10 Claims, 6 Drawing Sheets

SENSORS AND SENSOR INTERFACE SYSTEMS

BACKGROUND

Embodiments relate to sensor systems and, in particular, interfaces for sensor systems.

Some sensors can use resistivity to indicate sensed information. For example, a thermistor can indicate a sensed temperature through its resistance. A circuit can be used to measure the resistance. A vehicle can include multiple such sensors, such as temperature sensors for intake air, exhaust, coolant, or the like.

BRIEF DESCRIPTION OF THE DRAWINGS

The description herein makes reference to the accompanying drawings wherein like reference numerals refer to like parts throughout the several views, and wherein.

DETAILED DESCRIPTION

Embodiments will be described with reference to the drawings. Although particular embodiments will be described, the scope of the following claims is not limited to these embodiments. In contrast, alterations, modifications, combinations, or the like can be made.

Figure 1:
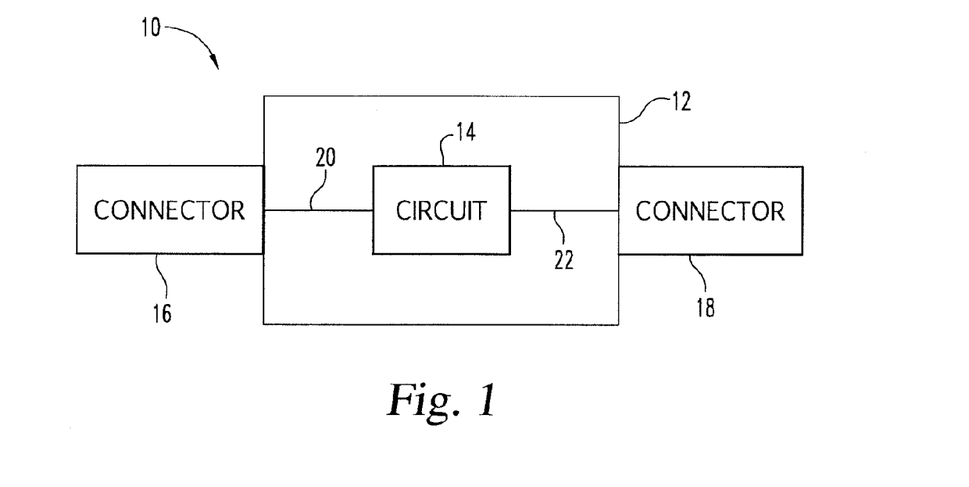
FIG. 1 is a block diagram illustrating a sensor interface module according to an embodiment.

FIG. 1 is a block diagram illustrating a sensor interface module according to an embodiment. In an embodiment, the sensor interface module 10 includes a housing 12. The housing 12 can be configured to substantially encapsulate a circuit 14. A first connector 16 and a second connector 18 are coupled to the housing 12. In an embodiment, the connectors 16 and 18 can be coupled to the housing 12 by wires or other conductors. In another embodiment, the connectors can include connector housings that are integrally formed with the housing 12. In another embodiment, the connectors 16 and 18 can include connector housings that are mechanically attached to the housing 12. The connectors 16 and 18 can be coupled to the housing 12 using any combination of such techniques or similar techniques.

The connectors 16 and 18 can each include a plurality of contacts. The connectors 16 and 18 can have a same or different number of contacts. The circuit is electrically connected to at least one of the contacts of the first connector 16 and at least one of the contacts of the second connector 18. Connections 20 and 22 represent connections between the contacts of the connectors 16 and 18 and the circuit 14.

In an embodiment, the circuit 14 can be configured to generate an output signal in response to a sensed resistance. The circuit 14 can be coupled to one or more contacts of the first connector 18. Through the first connector 18, the circuit 14 can be coupled to a sensor and, in particular, a resistance based sensor. For example, the first connector 18 can include two contacts that are coupled to the sensor. A resistance sensed between the two contacts can be interpreted as a signal from the sensor. The circuit 14 can be configured to generate the output signal based on the sensed resistance. Although two contacts have been described, any number of contacts can be used to sense the resistance. For example, a single contact can be used with a node common to the circuit 14 and the sensor. In another example, the sensor can include a bridge circuit with multiple associated contacts. The circuit 14 can be coupled to contacts of the first connector 18 to supply a bias voltage, sense an output voltage, or the like.

Figure 2:
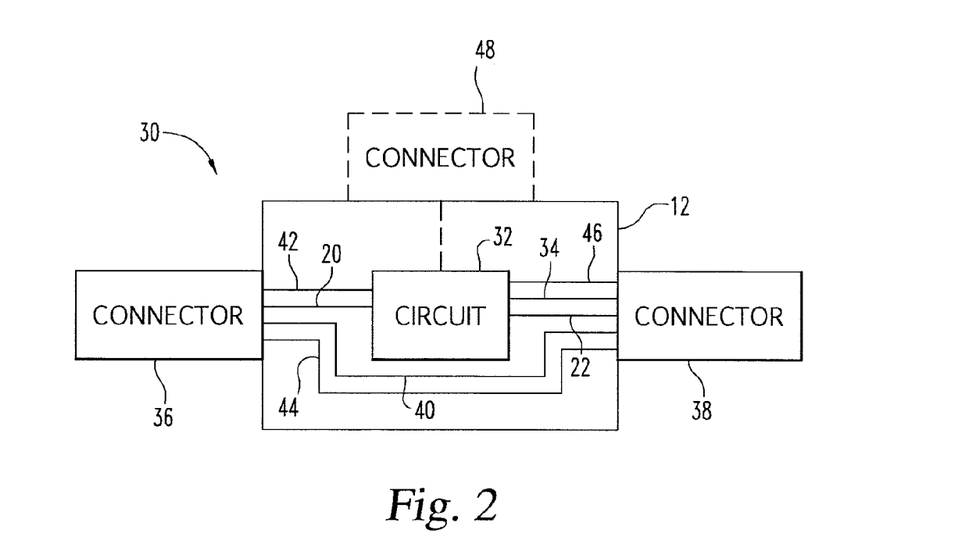
FIG. 2 is a block diagram illustrating a sensor interface module according to another embodiment.

FIG. 2 is a block diagram illustrating a sensor interface module according to another embodiment. In an embodiment, multiple connections can terminate and/or pass through the housing 12. For example, as will be described in further detail below, the second connector 38 can be coupled to a control module. Through the connector 38, a power connection 34 can be supplied. In addition, a common node, such as a ground 46 can be supplied.

Furthermore, one or more connections between the connectors 36 and 38 can be made. For example, a particulate matter sensor can include a heater configured to regenerate the sensor. The connections 40 and 44 can be pass-through connections for such a heater connection. However, in another embodiment, a common node can be shared among a pass-through connection, the sensor, the circuit, a power supply, a combination of such connections, or the like.

In an embodiment, a connection to a sensor includes connections 20 and 42. For example, connection 20 can be used for a sensor signal. Connection 42 can be a common node coupled to a common node 46 of connector 38. In another embodiment, connection 42 can be another sensor node, for example, of a differential pair. The module 30 can include any such connections, common nodes, pass-through connections, or the like.

In an embodiment, the connection 40 can be a direct connection. For example, a wire can be directly connected to contacts of the connectors 36 and 38. However, the connection 40 can be formed in other ways. For example, the connection 40 can include a part of the circuit 32. The connectors 36 and 38 can be soldered to a trace on a circuit board of the circuit 32.

In an embodiment, a number of contacts of the first connector 36 can be different from a number of contacts. As described above, each of the first connector 36 and second connector 38 can include multiple contacts. However, all of the contacts of the second connector 38 may not be used in the first connector 36. For example, the first connector 36 can have four contacts, two for a sensor input and return, 20 and 42, and two for a heater of the sensor, 40 and 44. The second connector 38 can have two contacts for a heater of the sensor, 40 and 44, an output signal 22, and power supply connections 34 and 46.

In an embodiment, the connectors 36 and 38 can be opposite gender connectors. As will be described below, the module 30 can be used in a vehicle control system. By using the same connector with opposite genders, the module 30 can be placed in line with an existing sensor connection. Power, other signals, other controls, or the like can be transferred to the circuit 32 through the connector 38, a third connector 48, or the like. Accordingly, existing control systems having a sensor connection that has degraded or has the potential to degrade can be retrofit with the module 30, making the sensing system more tolerant of variations and extending the useful life.

Figure 3:
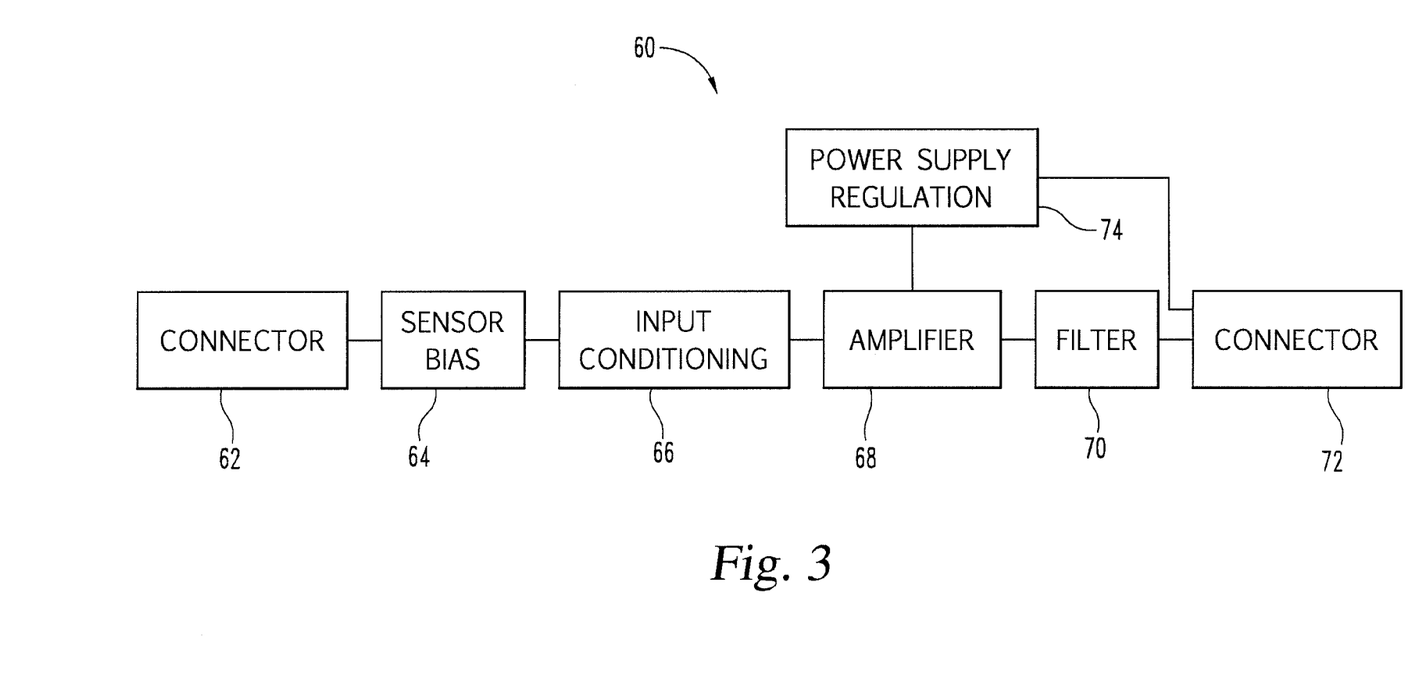
FIG. 3 is a block diagram illustrating a buffer of a sensor interface module according to an embodiment.

FIG. 3 is a block diagram illustrating a circuit of a sensor interface module according to an embodiment. In this embodiment, a first connector 62 can be configured to be coupled to a sensor. For example, the first connector 62 can be a connector configured to mate with a corresponding connector of a sensor. The circuit 60 can include a sensor bias circuit 64 associated with a target sensor. For example, the sensor bias circuit 64 can include a pull-up resistor to create a resistive divider with a resistive sensor. In another example, the sensor bias circuit 64 can include a bridge circuit. Any bias or interface circuit can be used as appropriate to the target sensor.

The circuit 60 can include input conditioning 66. For example, the input conditioning 66 can include over-voltage protection, reverse voltage protection, short circuit protection, or the like. In addition, the input conditioning 66 can include input offset mitigation circuitry.

The circuit 60 can include an amplifier 68. The amplifier 68 can be configured to scale, level-shift, limit, perform a combination of such functions, or the like. In an embodiment, the amplifier 68 can include a relatively low impedance output. Thus, for a resistivity based sensor, variability in connectors, wiring, or the like that can add parasitic resistance will likely be higher than the output impedance of the amplifier 68. Such parasitic effects will have a reduced effect on an output sensor signal.

In an embodiment, the circuit 60 can include filter 70. For example, the filter 70 can be a low pass filter; however, in other embodiments, the filter 70 can be a high-pass, band-pass, all-pass, notch filter, or the like according to the sensed signal and/or desired characteristics of the signal.

Although illustrated as discrete blocks with individual connections, the function of the various circuitry of the circuit 60 could be combined, distributed, or the like. For example, the sensor bias 64, input conditioning 66, amplifier 68, and filter 70 can be combined together into an aggregate amplifier circuit.

Figure 4:
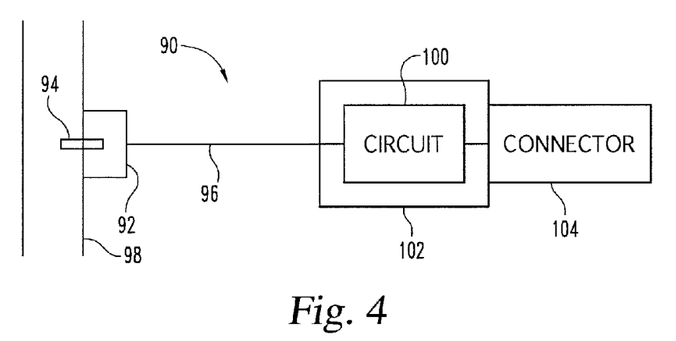
FIG. 4 is a block diagram illustrating a sensor according to an embodiment.

FIG. 4 is a block diagram illustrating a sensor according to an embodiment. In this embodiment, a sensor 90 is disposed with a sensor element 94 in fluid communication with a channel 98. For example, the channel 98 can be part of an exhaust system of a vehicle. The sensor element 94 can include a resistivity based particulate matter sensor. The sensor element 94 can be disposed at least in part in a housing 92.

A circuit 100 can be disposed in a second housing 102. In particular, the circuit 100 can be substantially encapsulated in the second housing 102. A connector 104 can be coupled to the second housing 102. The connector 104 can be coupled to the second housing 102 similar to connector/housing couplings described above. For example, the second housing 102 can be a separate housing or part of a housing of the connector 104. A conductor 96 is coupled to the housings 92 and 102. The circuit 102 is electrically connected to the sensor element 94 through the conductor 96.

The conductor 96 can be coupled to the housings 92 and/or 102 in a variety of ways. For example, the conductor 96 can be coupled to a housing 92 and/or 102 through a strain relief such as a resin, a clamp, a boot, a strap, or the like. In an embodiment, no connectors are present between the sensor element 94 and the circuit 100.

The circuit 100 can be configured to generate an output signal based on the sensor element 94 in response to a signal received through the conductor 96. For example, as described above, the sensor element 94 can be a resistive sensor element. The circuit 100 can be configured to sense a resistance of the sensor element 94 and generate an output signal accordingly.

Although one conductor 96 has been described, any number of conductors can be used as desired. Any input or output associated with the sensor element 94, associated components, or the like can include associated conductors. For example, as described above, two conductors can be associated with a heater for the sensor element 94 and two conductors can be associated with the sensor element 94 itself. In another example, any connection through a first connector 16, 36, or the like described above can be routed from the first housing 92 to the second housing 102 without intervening connectors.

In an embodiment, the sensor 90 can be used to retrofit existing installed sensors. For example, the connector 104 can be configured to have substantially the same configuration as a sensor to be replaced. If additional connections, such as a connector for power and or other signals is desired, a connector similar to connector 48 described above can be used.

Although a particulate matter sensor has been used as an example, other types of sensors can be used with the circuit 100. Any sensor with a relatively high resistivity can be used with the circuit 100. For example, the sensor can include a pressure sensor configured to sense a pressure due to small resistance changes in material with a relatively large quiescent magnitude. In another example, the sensor can include a thermistor with a relatively high resistance for an expected temperature in operation.

Figure 5:
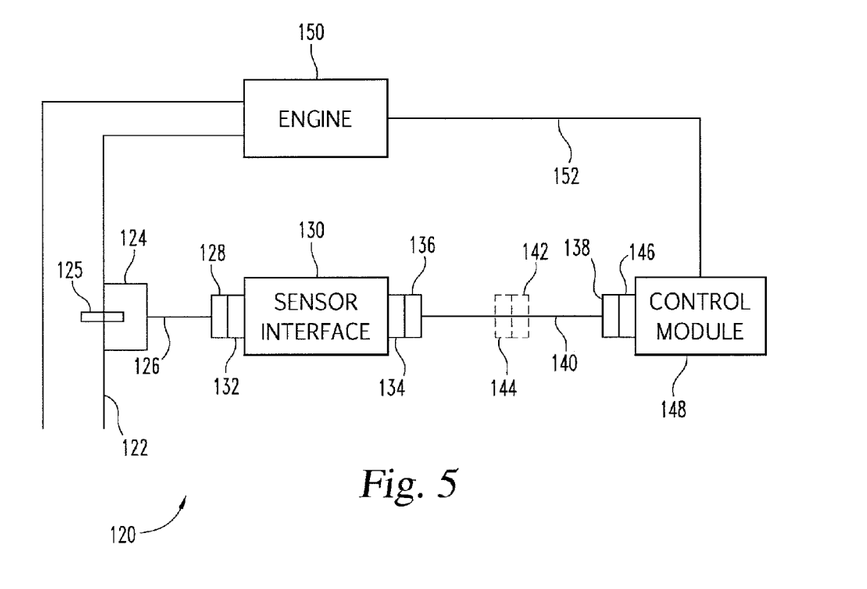
FIG. 5 is a block diagram illustrating an engine control system according to an embodiment.

FIG. 5 is a block diagram illustrating an engine control system according to an embodiment. In this embodiment, the control system 120 includes a sensor 124 having a cable 126 and a connector 128. The sensor is disposed in fluid communication with channel 122. As described above, the channel 122 can be an exhaust system of the engine 150 and the sensor 124 can be a particulate matter sensor.

A sensor interface module 130 can include connectors 132 and 134. The module 130 can be coupled to the sensor 124 through the connectors 128 and 132. In a particular embodiment, the connectors 128 and 132 can be directly connected. Thus, only a single connector pair is disposed between the sensor element 125 and a circuit of the module 130.

The module 130 is coupled to a control module 148 through wiring harness 140. The harness 140 can include multiple connectors. Connectors 136 and 138 are illustrated with examples of optional intervening connectors 144 and 142 illustrated in phantom. Any number of connector pairs can be present between the module 130 and control module 148. The control module 148 includes a connector 146 coupled to the connector 138 of the wiring harness 140.

The control module 148 can be coupled to an engine 150. For example, the control module 148 can be part of an engine management system. Control signals to and from the module 130 and/or other components can be processed by the control module 148. The control module 148 can be any variety of devices. For example, the control module 148 can be a dedicated controller configured to solely interact with the sensor 124. The control module 148 can have a communication interface such as a CAN bus interface to communicate with other control systems. In another example, the control module 148 can be an emission control computer of a vehicle. In another example, the control module 148 can be a controller for the entire vehicle including other non-emission related subsystems.

The module 130 can include a circuit, such as the circuit 14, 32, 60, or the like as described above. Accordingly, an effect of intervening connectors of the wiring harness 140 can have a reduced effect on a quality of the signal from the sensor 124.

In an embodiment, the module 130 can be configured to output a signal capable of driving an input of the control module 148 that is configured to expect an input from the sensor 124. For example, the control module 148 can have bias circuitry for biasing the sensor 124 if the module 130 was not installed. The module 130 can be configured to drive such an input. That is, even if a control module 148 is configured to be directly electrically coupled to a sensor 124, the module 130 can accommodate any such circuitry on the input of the control module 148 and/or emulate the sensor 124.

In another embodiment, the control module 148 can have reduced circuitry for processing an input from the sensor 124. For example, the module 130 can include a lower output impedance circuit. Accordingly, requirements for input offset currents and voltages associated with the control module 148 can be loosened. That is, the control module 148 can be designed with a greater variability and/or magnitude of input offset currents and voltages. For example, cost constraints, materials, and/or other design and manufacturing decisions can result in a control module 148 that has input characteristics that can make a connection to a high resistivity sensor difficult if not inoperable. The module 130 can allow such lower cost designs to be operable by increasing tolerance of such input offset effects.

In an embodiment, the output of the module 130 can be a signal that is similar to a signal output by the sensor 124. For example, a signal from the sensor 124 can be an analog signal. Similarly, the module 130 can be configured to output a corresponding analog signal. That is, the signal that is transmitted to the control module 148 can be an analog signal. In a particular embodiment, the signal is not digitized, packetized, or otherwise digitally processed; however, such functions, transformations, or the like can occur in the control module 148 or other similar circuitry.

As described above, the channel 122 can be part of an exhaust system. Accordingly, the sensor 124 can be exposed to relatively high heat. Some circuitry may not operate under such conditions. By placing the module 130 offset from the sensor 124 due to the cable 126, a reliability of the system 120 can be improved.

Figure 6:
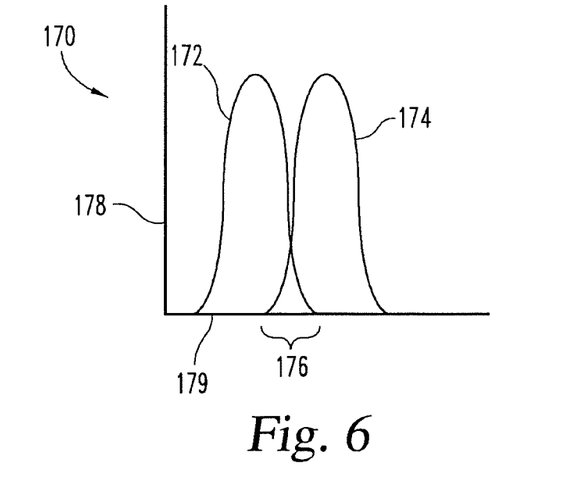
FIG. 6 is a graph illustrating a variability in sensed signals without a sensor interface.

FIG. 6 is a graph illustrating a variability in sensed signals without a sensor interface. Graph 170 illustrates a variability of output signals for two systems due to variability in components, operating conditions, and the like. Axis 178 represents a frequency of occurrence and axis 179 is an output level. Curve 172 represents a variability with ideal interconnects between a sensor and a controller, such as the sensor 124 and control module 148 of FIG. 5, but without the module 130.

In a particular example, a resistivity based sensor can have a substantially open circuit when no material is sensed. To distinguish between a clean sensor and a disconnected sensor, a resistor can be placed in parallel with the sensor. Thus, even when the sensor is a substantially open circuit, the resistance of the parallel resistor can be sensed. Curve 172 represents such a configuration with variability in the parallel resistor, components, or the like with ideal interconnections.

Curve 174 represents a variability considering the effect of interconnections between the sensor and a controller yet disconnected from a sensor. In an embodiment, connectors of wire harnesses can add parallel resistances. When a sufficient number of such parallel resistances are combined, the effective resistance can approach that of the intentionally added parallel resistance. Curve 174 represents such parasitic effects but with the sensor disconnected.

As illustrated curve 172 overlaps curve 174 in region 176. That is, a connected sensor cannot be distinguished from an unconnected sensor over the variability of components and conditions.

For example, a number of connector pairs can connect the sensor to the control module. Assuming that a connector can introduce a 100 MΩ resistance between terminals, with four connector pairs, eight 100 MΩ parasitic resistances are connected in parallel, resulting in approximately 12.5 MΩ parallel resistance. Such a resistance could be present even if the sensor is not connected.

A 10 MΩ open circuit detection resistor can be used. Accordingly, the parallel parasitic resistance can mask the intended parallel resistance. That is, as illustrated in FIG. 6, a variability of the parallel resistance can overlap with the parasitic parallel resistance. In this example, the minimum parallel parasitic resistance in normal operations can be represented by a lower end of the curve 174. Although the open circuit detection resistor can have a nominal value of 10 MΩ, the resistance could vary over particular operating conditions and component variability to be greater than 12.5 MΩ. To increase the lower limit of the parallel parasitic resistance, a number of connections can be reduced; however, this can place an upper limit on connections for a sensor.

Figure 7:
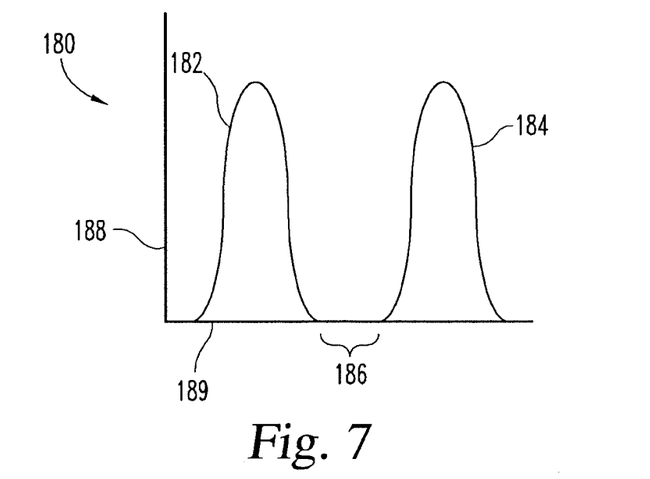
FIG. 7 is a graph illustrating a variability in sensed signals with a sensor interface according to an embodiment.

FIG. 7 is a graph illustrating a variability in sensed signals with a sensor interface according to an embodiment. Similar to FIG. 6, graph 180 illustrates the variably with axis 188 representing occurrence and axis 189 representing the output level. In this example, a module such as the module 130 described above is used. Curve 182 represents the sensor with a parallel resistivity. Curve 184 represents a disconnected sensor.

In particular, a gap 186 is introduced. A threshold can be established to decide whether the sensed value indicates a connected or disconnected sensor. Since less parasitic components are disposed between a sensor and module, an effect on the output of the module by the parasitic components is reduced. Furthermore, the lower impedance output of a module can reduce an effect of subsequent parasitic components.

In an embodiment, the module 130 can aid in diagnosing problems in a sensor system. For example, a megaohm meter may be needed to measure the sensor resistance if it is directly. In addition the sensor wiring may need to be checked to determine if a particular resistance measurement is due to deteriorated wiring. With the module 130 or similar modules, a measurement can be made at the output of the module 130 reducing a need for a megaohm meter and the parasitic resistance of sensor wiring need not be measured as the output of the module 130 can tolerate parasitic resistances that may require a megaohm meter to diagnose.

Figure 8:
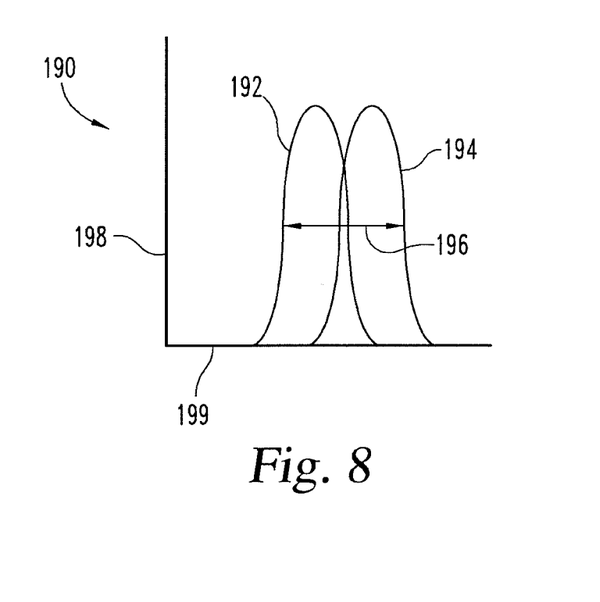
FIG. 8 is a graph illustrating another variability in sensed signals without a sensor interface.

FIG. 8 is a graph illustrating another variability in sensed signals without a sensor interface. Graph 190 again represents an occurrence axis 198 versus an output axis 199. Curve 192 represents a system without a module, and an example of variability considering worst case conditions. Curve 194 represents an example considering ideal conditions. Note that in this case, the sensor is connected for both curves. Total width 196 corresponds to a potential variability in the output from ideal to worst case conditions.

Figure 9:
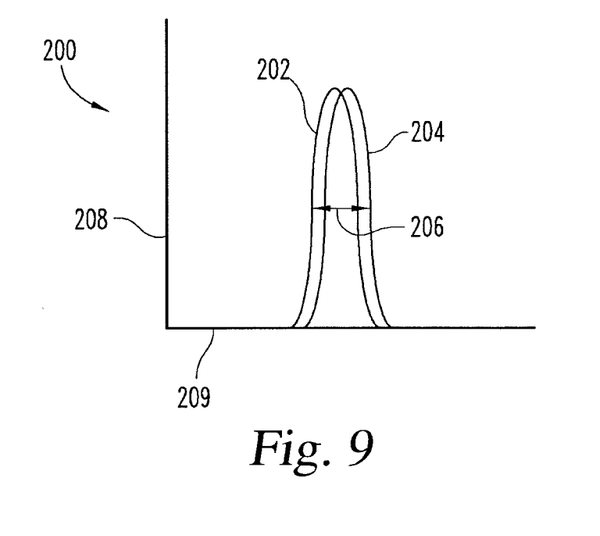
FIG. 9 is a graph illustrating another variability in sensed signals with a sensor interface according to an embodiment.

FIG. 9 is a graph illustrating another variability in sensed signals with a sensor interface according to an embodiment. Graph 200 again represents an occurrence axis 208 versus an output level axis 209. Curve 202 represents an example of worst case conditions while curve 204 represents an example of ideal conditions. However, in contrast to FIG. 8, a module as described above is present. Accordingly, not only is a variability within ideal conditions reduced, but a variability between worst case and ideal conditions is reduced.

Figure 10:
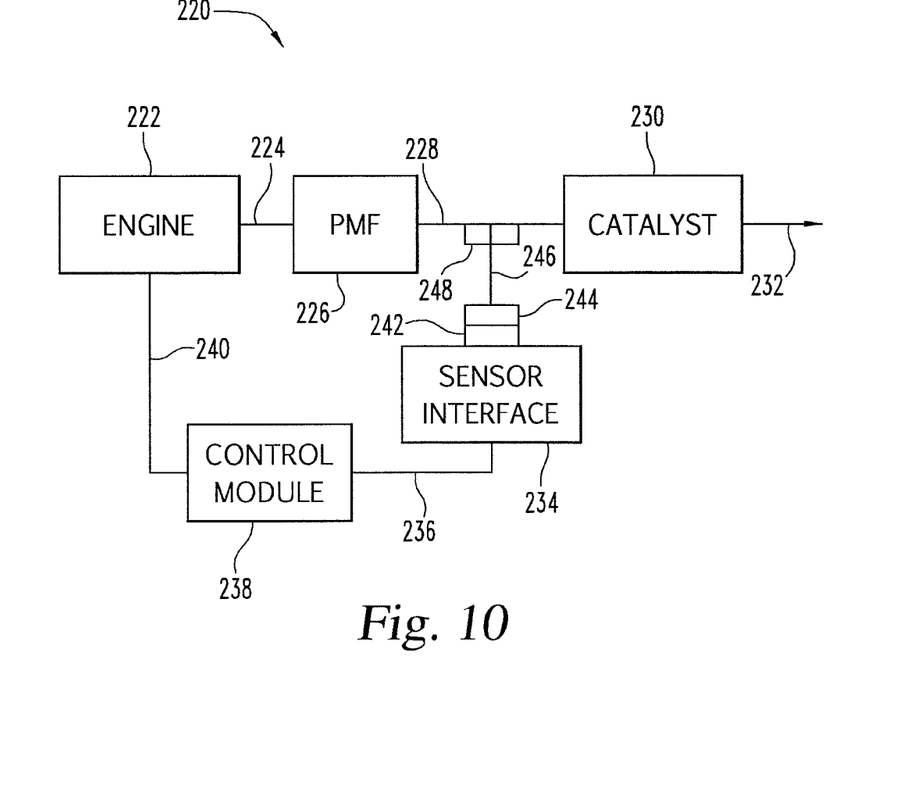
FIG. 10 is a block diagram illustrating an engine system including an after-treatment system according to an embodiment.

FIG. 10 is a block diagram illustrating an engine system including an after-treatment system according to an embodiment. In this embodiment, the engine system 220 includes an engine 222 coupled to a particulate matter filter 226 through an exhaust channel 224. The particulate matter filter 226 can be coupled to a catalyst system 230 through channel 228. For example, the catalyst system 230 can include a diesel exhaust fluid system and a selective catalyst reduction system. However, other types of catalyst systems can be used.

A sensor 248 is disposed in channel 228. The sensor 248 is coupled to a sensor interface 234 through cable 246 and connectors 242 and 244. The connection between the sensor 248 and sensor interface 234 can be as described above. Thus, the sensor signal 236 can be provided to the control module 238 and be in control of the engine 240. Accordingly, the reliability of the system 220 can be improved.

Although the sensor 248 is illustrated as coupled to channel 228, the sensor 248 can be coupled to other locations upstream or downstream of the particulate matter filter 226. For example, the sensor 248 could be coupled to channel 232 downstream of the catalyst system 230, or other downstream component. In another example, the sensor 248 could be coupled to the channel 224, upstream of the particulate matter filter 226. Moreover, multiple such sensors 248 can be present in the system in various locations, each with a corresponding circuit as described above.

While embodiments have been described with reference to the drawings, the sprit and scope of the following claims is not limited to the disclosed embodiments, but on the contrary, is intended to cover various modifications, combinations, and equivalent arrangements. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

The invention claimed is:

1. An apparatus, comprising:
a housing;
a first connector coupled to the housing and having a first plurality of contacts;
a second connector coupled to the housing and having a second plurality of contacts; and
a circuit electrically connected to at least one of the first plurality of contacts and at least one of the second plurality of contacts;
wherein:
the circuit is encapsulated within the housing, and
the circuit is configured to generate an output signal in response to a resistance sensed between two of the first plurality of contacts.

2. The apparatus of claim 1, wherein the first connector and the second connector are directly connected to the housing.

3. The apparatus of claim 1, wherein at least one of the first plurality of contacts is directly electrically connected to at least one of the second plurality of contacts.

4. The apparatus of claim 1, wherein a number of the first plurality of contacts is different from a number of the second plurality of contacts.

5. The apparatus of claim 1, wherein the first plurality of contacts include a contacts for a sensor input and a contact for a sensor return, and two contacts for a sensor heater.

6. The apparatus of claim 5, wherein the second plurality of contacts include contacts for each of a sensor output, a power supply, and a common node, and two contacts for a sensor heater.

7. A system, comprising:
a module having a first connector having a first plurality of contacts and a second connector having a second plurality of contacts, the module including:
a housing;
a first connector coupled to the housing and having a first plurality of contacts;
a second connector coupled to the housing and having a second plurality of contacts; and
a buffer electrically connected to at least one of the first plurality of contacts and at least one of the second plurality of contacts;
wherein the buffer is encapsulated within the housing;
a sensor including a third connector having a third plurality of contacts;
wherein the first connector is directly connected to the third connector.

8. The system of claim 7, further comprising a plurality of wires directly connected between the sensor and the third connector.

9. The system of claim 7, further comprising:
a control module including a fourth connector;
a wiring harness coupled between the second connector and the fourth connector;
wherein:
the wiring harness includes at least one connector pair disposed between the second connector and fourth connector; and
the connector pair includes conductors associated with the second plurality of contacts.

10. The system of claim 1, further comprising a sensor including a third connector having a third plurality of contacts, wherein the first connector is directly connected to the third connector.

* * * * *